United States Patent [19]

Nowak et al.

[11] Patent Number: 4,699,616

[45] Date of Patent: Oct. 13, 1987

[54] CATHETER RETENTION DEVICE AND METHOD

[75] Inventors: George M. Nowak, Lake Villa; James A. Stupar, Crystal Lake, both of Ill.

[73] Assignee: Hollister Incorporated, Libertyville, Ill.

[21] Appl. No.: 874,293

[22] Filed: Jun. 13, 1986

[51] Int. Cl.⁴ ............................................ A61M 25/02
[52] U.S. Cl. ............................ 604/180; 128/DIG. 26
[58] Field of Search ....................... 128/DIG. 26, 133; 604/174, 179, 180

[56] References Cited

U.S. PATENT DOCUMENTS

| | | | |
|---|---|---|---|
| 2,586,940 | 2/1952 | Graham | 128/DIG. 26 |
| 3,138,158 | 6/1964 | Gordon | 128/214 |
| 3,682,180 | 8/1972 | McFarlane | 128/350 |
| 3,683,911 | 8/1972 | NcCormick | 128/214 |
| 4,040,427 | 8/1977 | Winnie | 128/DIG. 26 |
| 4,077,412 | 3/1978 | Moossun | 604/174 X |
| 4,261,363 | 4/1981 | Russo | 128/350 |
| 4,360,025 | 11/1982 | Edwards | 604/180 |
| 4,392,854 | 7/1983 | Ibach | 604/174 |
| 4,392,857 | 7/1983 | Beran | 128/DIG. 26 |
| 4,490,141 | 12/1984 | Lacko | 604/180 |

FOREIGN PATENT DOCUMENTS 653436 11/1937 Fed. Rep. of Germany ... 128/DIG. 26
2147811A 5/1985 United Kingdom .

Primary Examiner—Dalton L. Truluck
Attorney, Agent, or Firm—Tilton, Fallon, Lungmus

[57] ABSTRACT

A device for retaining a catheter in place at its point of entry into a patient's body. The device includes a resilient, adhesive barrier pad having an opening intended to be aligned with the fenestration in the body wall, the pad also having an entry slit leading to that opening, and a one-piece molded plastic support structure that includes a base secured to the pad, two (or more) flexible support arms projecting upwardly from the base at opposite sides of the pad opening, and a pair of elongated clamping bars at the upper ends of the support arms. In use of the device, a catheter is guided laterally through the entry slit to the opening of the barrier pad, the resilient pad is then adhesively secured to the patient with the edges of the pad defining the slit urged tightly together, and the clamping bars are latched together with the catheter clamped securely therebetween. The method of forming such a catheter retention device is also disclosed.

22 Claims, 10 Drawing Figures

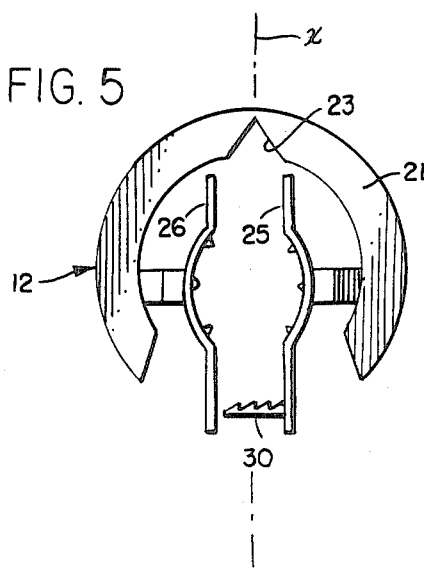
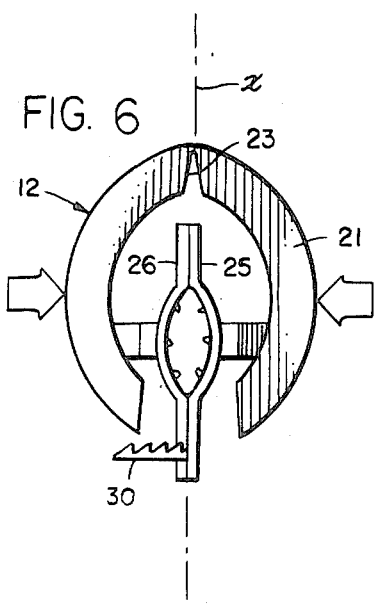
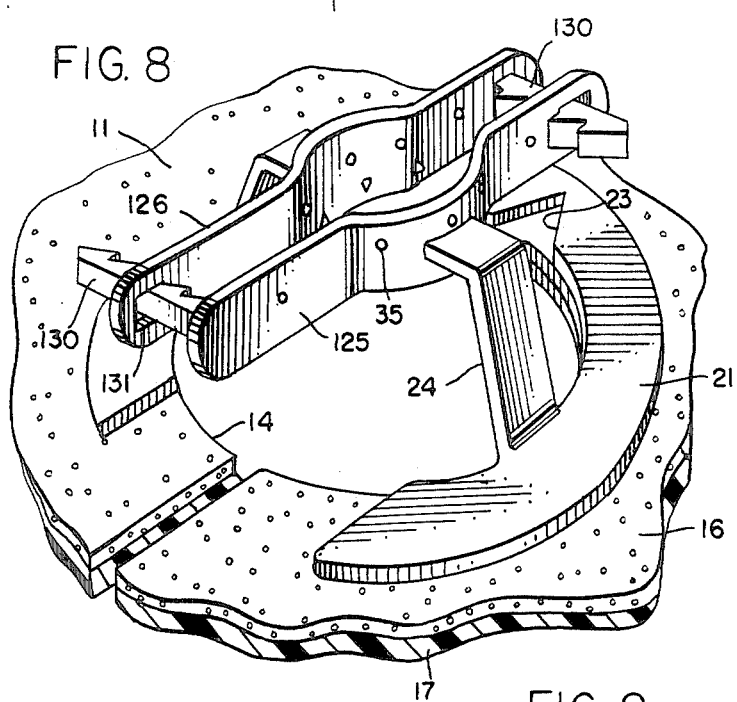
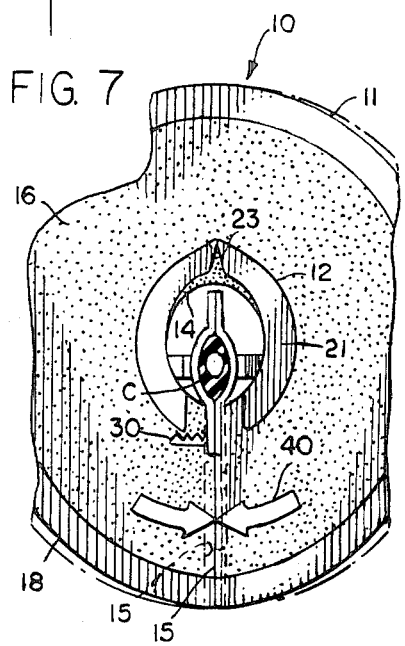
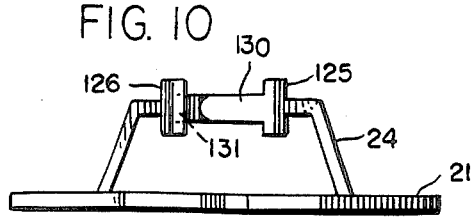
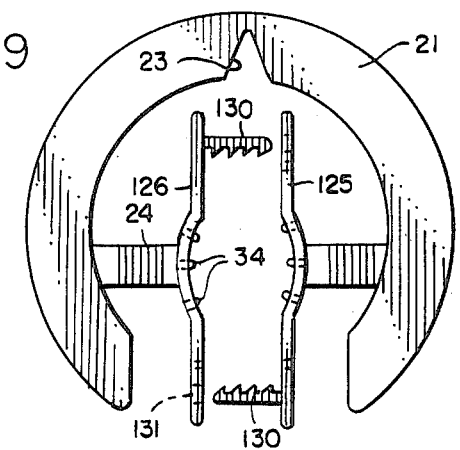

CATHETER RETENTION DEVICE AND METHOD

BACKGROUND AND SUMMARY

While it is apparent that catheters for post-surgical drainage and other medical purposes should be securely positioned so that they are not inadvertently dislodged or withdrawn by patient movement or by bedside activities of physicians and hospital staff, and while it is apparent that the wound or incision area, including the skin surrounding the point of entry, should be protected against the irritating and excoriating effects of fluid contact, prior devices have generally fallen far short of achieving such objectives, at least without introducing additional problems that offset the improvements. For example, to help immobilize an indwelling catheter, it is a common practice to suture the catheter to a retention device and also suture the retention device to a patient's skin. The former does not always insure against catheter movement, and the latter may result in irritation, infection, and considerable patient discomfort over the typical period of catheter placement (usually 5 to 7 days). Thus, in published UK application No. 2,147,811A, sutures are shown for the purpose of securing the device to the patient's skin, although the use of adhesives is also mentioned. In U.S. Pat. No. 4,392,854, adhesive tape may be used to hold the device in place but sutures are indicated for connecting the catheter to the supporting device.

Other catheter retention devices are disclosed in U.S. Pat. Nos. 4,360,025, 4,261,363, 3,138,158, 3,682,180, and 4,490,141. The use of adhesives is frequently disclosed for attaching a retention device to a patient's skin, but in some cases the retaining devices block medical inspection of the wound or incision, and in other cases the catheters are not supported at generally right angles (normal to) the surface of the skin. In still other instances, attachment of the supporting devices is relatively awkward and inconvenient, increasing the possibilities of patient discomfort. Thus, a construction that requires a catheter to be threaded through an opening in the supporting device for application or removal of that device is believed undesirable. In general, while a variety of catheter retention devices have been disclosed in the art, and while some of them have advantageous features, all of them are believed to have one or more serious shortcomings involving construction, operation, and/or effectiveness in use.

An important aspect of this invention therefore lies in providing an improved catheter retention device that is simple in construction and reliable in operation, may be securely attached to a patient without sutures, without threading the catheter through the device, and without obstructing visual inspection of the site after the device is in place, and is easily manipulated to clamp and immobilize a catheter and, if necessary, permit selective repositioning of the catheter in relation to the device. Furthermore, the device supports the catheter so that it extends at right angles to the skin at the entry point, protects the skin over a wide surrounding area, and at the same time exposes the immediate area of the incision or wound for direct visual inspection. The device may be easily manipulated by one hand, leaving the physician's other hand free for positioning the catheter or for performing other operations. Because of the security of the attachment between the device and the catheter, sutures connecting the two are unnecessary, but the retention device is designed to permit the use of such sutures in those exceptional circumstances where supplementary suturing is desired.

In brief, the device takes the form of an apertured, flexible, and resilient adhesive barrier pad upon which a molded plastic catheter support structure is mounted. An entry slit leads from the periphery of the pad to its central aperture or opening. The support structure includes an arcuate base affixed to the pad, a pair of spaced flexible support arms formed integrally with the base and projecting upwardly at opposite sides of the opening, and a pair of elongated clamping bars joined at intermediate points along their lengths to the upper ends of the flexible support arms. In a preferred embodiment, the bars are permanently joined together at one of their ends, have ratchet coupling means at their opposite ends, and have their axes askew so that the ratchet elements are disaligned and uncoupled when the device is supplied to a user. However, since the latching bars extend along parallel planes and are disposed in contiguous relation in an untensioned state, they are already in a relationship that approximates their closed condition and, when finally shifted into closed positions during use, have no internal forces or stresses urging them to spring apart into unlatched condition and exert no shear stresses at the interface between the support structure and pad.

Such a construction allows a user to position a catheter through the opening of the barrier pad by spreading the edges of the pad defining the entry slit, then simply urging the catheter laterally through that slit to the opening, and finally urging the edges of the slit together while at the same time adhesively securing the pad to the patient. The sealant barrier material of the pad joins together to close the slit and provide a continuous or uninterrupted annular barrier zone about the exit site, thereby protecting the surrounding skin from the excoriating effects caused by contact with exudate. In a preferred embodiment, the barrier material of the pad is covered with a layer of resilient foam to which the base of the support structure is secured. During the steps of closing the slit and adhesively securing the pad to a patient's skin, the edges of the resilient foam layer are also brought into contact with each other thereby enhancing the protection afforded by the pad. To facilitate closing of the slit during the steps of applying the pad, the base of the support structure is provided with a notch facing the inner end of the slit, the notch allowing the sections of the base on opposite sides of the slit to be urged together as the barrier pad is re-formed to close the slit and adhere the pad to the patient's skin.

Other features, objects, and advantages of the invention will become apparent from the specification and drawings.

DRAWINGS

FIG. 5 is a top plan view of the support structure of the device in its original molded condition.

FIG. 6 is a plan view similar to FIG. 5 but showing the subsequent step in the fabrication of the catheter retention device.

FIG. 7 is a fragmentary top plan view of the device, shown in reduced scale, illustrating the steps of closing the slit of the pad in connection with adhering the pad to a patient.

FIG. 8 is a perspective view depicting a second embodiment of the invention.

FIG. 9 is a top view of the embodiment of FIG. 8.

FIG. 10 is a front view of the embodiment of FIG. 8.

DETAILED DESCRIPTION OF PREFERRED EMBODIMENTS

Figure 1:
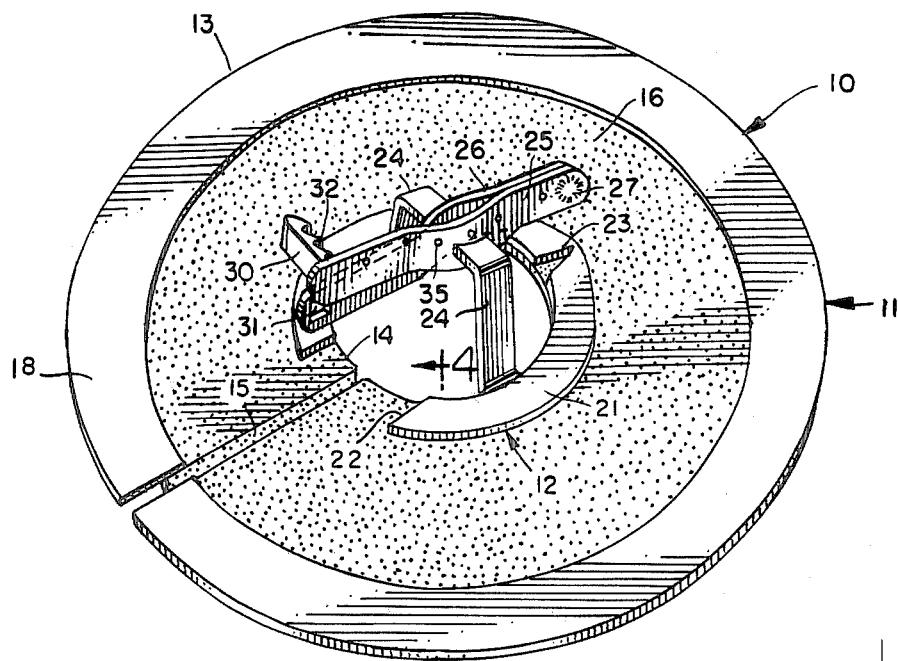
FIG. 1 is a perspective view of a catheter retention device in the form it could be supplied to a user (with outer wrapping or packaging removed).

Referring to the embodiment depicted in FIGS. 1-7, the numeral 10 generally designates a catheter retention device composed of a barrier pad 11 and a catheter support structure 12. The pad is planar and has a generally circular periphery 13 although other shapes may be selected. An opening 14 is provided at or near the center of the pad and a radial entry slit 15 extends between that opening and the pad's outer periphery.

Figure 4:
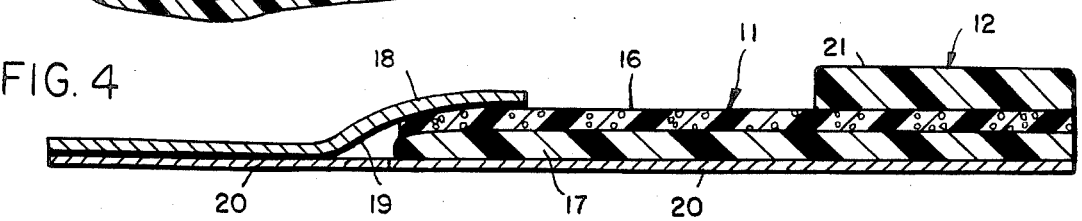
FIG. 4 is a somewhat schematic enlarged sectional view taken along line 4—4 of FIG. 1.

The materials and construction of the pad may be varied considerably as long as the thin, planar pad is flexible and therefore generally conformable with body contours, is sufficiently deformable to permit the edges of slit 15 to be brought into tight contact with each other, and is provided along its underside with a suitable pressure-sensitive adhesive material that not only immobilizes the pad on the patient's skin but, preferably, also performs a sealing function in protecting the skin against fluid contact. A particularly advantageous construction is depicted in the drawings where pad 11 is shown to be composed of a top layer 16 of resilient, flexible, fine-celled thermoplastic foam (such as a polyolefin or polyurethane foam), a lower layer 17 of soft, tacky, and deformable skin barrier material (such as karaya or a barrier composition of the type designated as "Hollihesive" by Hollister Incorporated, Libertyville, Ill.), and a surrounding layer 18 of a suitable microporous material (such as the gas-permeable but liquid-barrier non-woven microporous material disclosed in U.S. Pat. No. 4,213,458). The underside of the surrounding microporous layer 18 is coated with any suitable medical-grade pressure-sensitive adhesive 19, such as a hypo-allergenic acrylic adhesive commonly used in medical applications. The pressure-sensitive adhesive of the microporous border layer 18, and the tacky surface of barrier layer 17, may be covered by removable silicone-coated release sheets 20 (FIG. 4).

The catheter support structure 12 is molded in one piece from any suitable polymeric material having the requirements of flexibility, toughness, and durability. Nylon has been found effective, but other thermoplastic materials such as polysulfone or polycarbonate may be used.

Support structure 12 comprises an arcuate or curved planar base 21 secured to the upper surface of pad 11 about central opening 14. The base is interrupted at 22 with its ends spaced equally on opposite sides of slit 15 in the pad. Diametrically opposite from the interrupted zone, and from slit 15, is a V-shaped notch 23 that extends outwardly from the inner periphery of the arcuate planar base.

A pair of flexible support arms 24 project upwardly from the base at opposite sides of the opening 14 and from points spaced equally from a vertical mid plane x extending through slit 15 and V-shaped notch 23. Each arm has an upstanding portion 24a and, at its upper end, an inwardly-turned portion 24b. The inwardly-turned portions of the two arms merge with a pair of elongated clamping bars 25 and 26. As shown most clearly in FIGS. 2 and 3, the clamping bars extend along, and are generally disposed on opposite sides of, the same vertical mid plane that passes through slit 15 and notch 23. The bars are spaced a substantial distance above opening 14 and generally extend in the same direction as the plane of pad 11. Each bar is in the form of a thin horizontally-elongated strip having a width (measured vertically) substantially greater than its thickness. It will also be observed that each of the clamping bars has planar end portions 25a, 26a and arcuate intermediate portions 25b, 26b that together define an aperture for receiving and holding a portion of a catheter C in a direction perpendicular or normal to the plane of pad 11.

Figure 3:
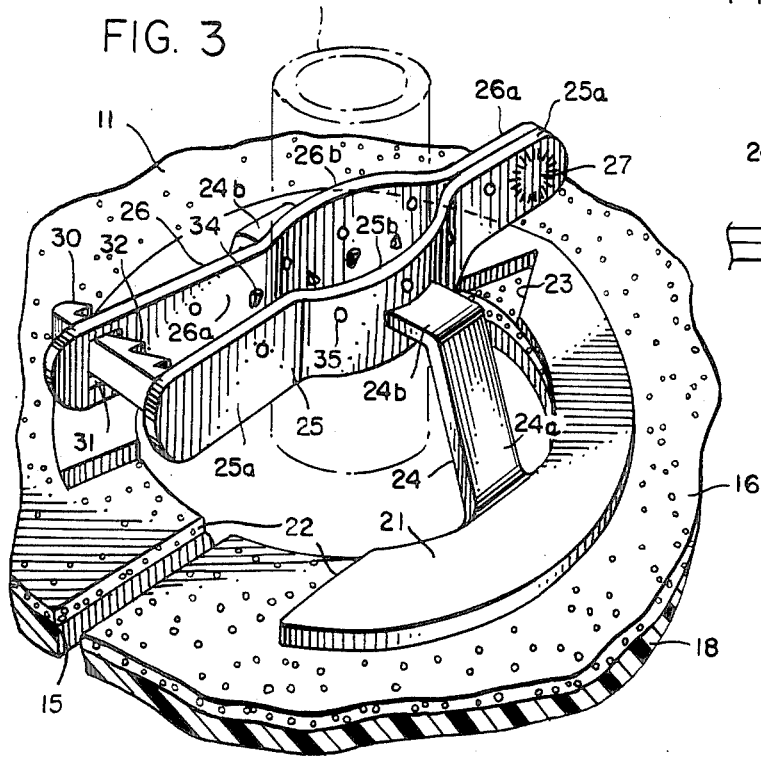
FIG. 3 is an enlarged perspective view similar to FIG. 1 but showing the relationship of the clamping jaws when the device is in use.

Means are provided for connecting the two bars together at their opposite ends when a catheter C is to be clamped in place as shown in FIG. 3. In the preferred embodiment shown, such connecting means includes a permanent connection at 27 between two corresponding end portions 25a and 26a of the clamping bars. The permanent connection may be in the form of a fusion bond, a heat seal, one-way snap fit, or some other form of secure interlock or interconnection between the parts. At their opposite or free ends, the clamping bars are provided with suitable latching means in the form of a ratchet 30 formed integrally with one of the bars 25 and a latching recess 31 formed in the end portion of the opposing clamping bar 26. The ratchet arm 30 of clamping bar 25 extends in the direction of the other bar 26, is receivable in aperture 31, and has a series of teeth 32 for holding the free ends of the clamping bars together in any of a variety of partially and fully closed positions.

Figure 2:
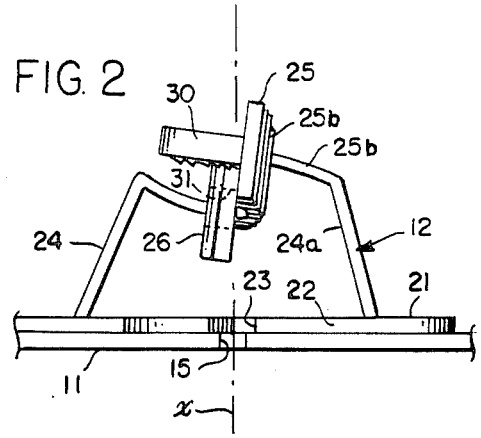
FIG. 2 is an enlarged end view illustrating details of the relationship as shown in FIG. 1.

Of particular significance is the fact that when the two bars have their ends joined together at permanent connection 27 they are disposed in contiguous relation, extending along mid plane x, but their longitudinal axes are slightly askew so that ratchet arm 30 does not extend through opening 31 but, as illustrated in FIGS. 1 and 2, extends over the top of edge of bar 26. Under such conditions, the clamping bars are generally untensioned. The result is that the clamping bars of the support structure are biased into closed positions, since any forces tending to separate the free ends of the bars will be resisted by restorative forces tending to urge free end portions 25a and 26a back into contiguous relation.

In use, the catheter retention device 10 would obviously be applied to a patient in which a catheter or drainage tube is already in place. The outer end of the catheter would ordinarily be connected to a receptacle or to some other medical equipment, so that threading the outer end of the catheter through opening 14 would be most inconvenient. Such problems are avoided by the present construction because a user may easily position the catheter in opening 14 by simply spreading apart the edges of slit 15 and then shifting the pad so that the catheter is moved laterally inwardly along the expanded slit to the central opening 14.

With the catheter extending through the opening of the pad and the uncovered adhesive surfaces of the pad disposed directly above the skin area surrounding the wound, the user simply urges the edges of the slit 15 together (in the directions represented by arrows 40 in FIG. 7) and simultaneously brings the adhesive surfaces of the barrier pad into contact with the patient's skin.

The flexible and resilient construction of the pad readily allows such limited deformation, and the notch 23 of base 21 insures that the base will not interfere with such closure of the slit 15. At the closed edges of the slit, the layer of karaya or other tacky sealant material merges or flows together to produce a continuous ring of protective barrier material about the wound. The edges of the foam layer 16 are also brought together and contribute to the protective effect by helping to maintain an uninterrupted sealing zone about the wound.

Catheter C is positioned in the aperture defined by the arcuate intermediate portions 25b and 26b of the clamping bars simply by spreading the free ends of the bars sufficiently to allow lateral placement of the catheter into position between arcuate portions 25b and 26b. The clamping bars are then closed (or allowed to close by reason of the restorative forces already described), except that the user first urges the free end of bar 26 upwardly, and the free end of bar 25 downwardly, to bring ratchet arm 32 into alignment with opening 31. The extent of clamping force is selectively controlled by latching the free ends together at any of the increments defined by teeth 32. In FIG. 7, the clamping bars are shown to be closed to their maximum extent.

To insure against sliding movement of the catheter with respect to the clamping arms, the arcuate inner surfaces of the intermediate portions 25b and 26b are provided with a plurality of small pointed lugs or barbs 34. It has been found that secure, highly effective retention is achieved by the clamping action described; however, should the physician decide that an additional need would be fulfilled by the use of sutures, openings 35 are provided in the clamping bars 25, 26 through which such sutures may be inserted and anchored.

Despite the fact that the clamping bars of the support structure are biased into closed positions, it has been found that such structure may still be molded in one piece following a sequence of steps indicated in FIGS. 5 and 6. FIG. 5 schematically illustrates the support structure 12 in the condition it is molded, with base 21 generally circular in outline and, more importantly, clamping arms 25 and 26 spaced well apart. Following such molding, the sides of the base (i.e., the portions of the base on opposite sides of vertical mid plane x) are urged towards each other until the clamping bars 25 and 26 are disposed in contiguous parallel relation (FIG. 6). As the clamping bars are brought together in this manner, they are simultaneously twisted slightly so that ratchet arm 30 will pass above (or below) the end portion 26a of bar 26. The opposite end portions of the respective bars are then permanently joined together and base 21 is sealed adhesively or by any other means to the upper surface of pad 11 to produce the final structure depicted in FIG. 1.

The embodiment of FIGS. 7–9 is similar to the device already described except for the construction of clamping bars 125 and 126 and the fact that such bars are biased into normally open positions rather than into closed or clamping positions. It will be noted that bars 125, 126 are not permanently joined at one end but instead are provided with ratchet assemblies 130, 131 at both ends. The device is used in the same manner already described, with the slitted barrier pad 11 being fitted about a catheter, its slit then being closed, but with squeezing forces being applied at both ends of the respective clamping bars for the purpose of clamping a catheter between the arcuate intermediate portions of the bars.

In the embodiments shown, central opening 14 in pad 11 is substantially larger in diameter than the width of slit 15. Specifically, opening 14 has a diameter that approximates the inside diameter of base 21. While such a size relationship is preferred, it is to be understood that the device might instead be supplied to a user with opening 14 of reduced size, possibly no greater in diameter than the width of slit 15, with the expectation that a nurse or doctor might, if desired, cut the pad to form a central opening of greater size to suit the particular catheter exit site.

While in the foregoing we have disclosed embodiments of the invention in considerable detail for purposes of illustration, it will be understood by those skilled in the art that many of these details may be varied without departing from the spirit and scope of the invention.

We claim:

1. A device for retaining a catheter in place at its point of entry into a patient's body, comprising a flexible planar barrier pad with an adhesive underside for attachment to a patient's skin; said pad having a generally central opening therethrough and a narrow entry slit with generally parallel, closely-positioned, opposing edges leading to said opening from the periphery of said pad; and a catheter support structure including a base secured to said pad and clamping means spaced above said opening for holding a portion of a catheter in generally coaxial relation with respect to said opening; said pad and base being deformable to permit the edges of said pad defining said slit to be separated sufficiently to allow a catheter to be advanced laterally through said slit into said opening and thereafter brought together into sealing engagement with each other just prior to adhesive attachment of said pad to a patient's skin; said pad including deformable upper and lower layers; said lower layer being formed of a resilient, pliable, skin barrier material having pressure-sensitive adhesive properties; said lower layer providing adhesive surfaces along the opposing edges of said slit for securing said slit in sealed condition when said edges are urged together; said base including a pair of base sections secured to said pad on opposite sides of said opening and on opposite sides of a projection of the longitudinal midline of said slit; said base sections being movable away from and towards each other as the edges of said pad defining said slit are spread apart and urged together, respectively; said catheter support structure also including a pair of flexible support arms projecting upwardly from said base sections; and said clamping means including a pair of mutually engageable clamping members at the upper ends of said arms.

2. The device of claim 1 in which said upper layer of said pad is formed of a fine-celled, resilient, thermoplastic foam.

3. The device of claim 1 in which said base is arcuate and said sections thereof are delineated by a notch facing towards said slit across said opening.

4. The device of claim 3 in which said notch is V-shaped.

5. A device for retaining a catheter in place at its point of entry into a patient's body, comprising a flexible planar barrier pad with an adhesive underside for attachment to a patient's skin; said pad having a generally central opening therethrough and an entry slit leading to said opening from the periphery of said pad; and a catheter support structure including a base secured to said pad and clamping means spaced above said opening for holding a portion of a catheter in generally coaxial relation with respect to said opening; said pad and base being deformable to permit the edges of said pad defining said slit to be separated sufficiently to allow a catheter to be advanced laterally through said slit into said opening and thereafter brought together into sealing engagement with each other just prior to adhesive attachment of said pad to a patient's skin; said catheter support structure also including a pair of spaced flexible support arms projecting upwardly from said base at opposite sides of said openings; said clamping means being provided at the upper ends of said arms and comprising a pair of elongated clamping bars joined at intermediate points along their lengths to the upper ends of said support arms; said bars being disposed alongside each other substantially above said opening of said pad and having intermediate portions with opposing recesses defining an aperture for receiving and holding a portion of a catheter in general coaxial relation with respect to said opening; and connecting means for connecting said bars to each other at their opposite ends.

6. A device for retaining a catheter in place at its point of entry into a patient's body, comprising a planar pad with an adhesive underside for attachment to the patient's skin; said pad having a generally central opening extending therethrough; a catheter support structure including a base secured to said pad, a pair of spaced flexible support arms projecting upwardly from said base at opposite sides of said opening, and a pair of elongated clamping bars joined at intermediate points along their lengths to the upper ends of said flexible support arms; said bars being disposed alongside each other substantially above said opening of said pad; and connecting means for connecting said clamping bars to each other at their opposite ends; said bars having intermediate portions with opposing recesses defining an aperture for receiving and holding a portion of a catheter in general coaxial relation with respect to said opening; said connecting means including selectively engagable latching means located at least at one of the ends of said clamping bars for facilitating insertion and removal of a catheter into and out of said aperture.

7. The device of claim 6 in which said latching means includes a toothed ratchet arm provided by one of said bars and a recess provided by the other of said bars for receiving said ratchet arm; the edges of said recess being engagable with the teeth of said ratchet arm for selective latching engagement therewith.

8. The device of claim 6 in which each of said latching bars has a first end and a second end; said latching means being located only at said first ends of said clamping bars; said bars being permanently joined together at their second ends.

9. The device of claim 8 wherein said first ends of said bars are normally in contiguous relation when said bars are untensioned and are movable away from each other into spread-apart positions for the insertion or removal of a catheter into or out of said aperture.

10. The device of claim 9 in which said first ends of said clamping bars are normally in contiguous but non-aligned positions with the longitudinal axes of the bars askew and with said ratchet arm of said one bar laterally disposed with respect to said other bar, whereby said bars may be spread apart at their first ends for aligning said ratchet arm with said recess when a catheter is to be received and clamped between said bars.

11. The device of claim 10 in which said base is arcuate and is provided with at least one notch extending outwardly from the inner periphery thereof.

12. The device of claim 6 in which said latching means is provided at opposite ends of said bars; said latching means at each end comprising a toothed ratchet arm provided by one of said bars and a recess provided by the other of said bars; said bars normally being spaced apart with said ratchet arms aligned with but spaced from said recesses; the edges of said recesses being engagable with the teeth of said ratchet arms for latching said bars together when the same are urged towards each other to clamp a catheter therebetween.

13. The device of claim 6 in which each of said clamping bars has a width, measured along a plane generally perpendicular to said pad, substantially greater than the thickness thereof.

14. The device of claim 13 in which said latching bars are provided with a plurality of openings therethrough for receiving ligature.

15. The device of claim 6 in which said intermediate portions of said latching bars are provided with a plurality of opposing barbs for engaging the wall of a catheter therebetween.

16. The device of claim 6 in which said pad includes an upper layer of fine-celled flexible plastic foam in sealing engagement with said base of said support structure.

17. The device of claim 16 in which said upper layer of foam is bordered by a microporous layer having an adhesive-coated undersurface.

18. The device of claim 16 in which a layer of tacky skin-barrier material extends along the underside of said upper foam layer.

19. The device of claim 6 in which said pad is provided with a slit extending from the outer periphery thereof to said central opening; said slit being generally aligned with said elongated clamping bars.

20. A method of making a catheter retention device having a pair of flexible plastic clamping bars that are joined together at one end, extend along generally parallel planes, and are provided with latching means at their opposite ends, comprising the steps of molding in one piece a support structure having an arcuate planar base defining an opening, a pair of flexible integral support arms projecting upwardly from said base at opposite sides of said opening, and a pair of spaced-apart clamping bars formed integrally with said arms at the upper ends thereof, said bars being elongated, generally parallel with said base, and each provided at a first end thereof with latching means; next urging said elongated bars together into contiguous parallel relation but with their axes askew so that second ends of said bars are in direct alignment but said first ends are disaligned with the latching means thereof in disengaged condition; then permanently securing said second ends of said bars together while they are disposed in contiguous relation with their axes askew.

21. The method of claim 20 in which said base is provided with a notch extending outwardly from the inner periphery thereof and located at a point intermediate the length of said base; said urging step including deforming said base in the plane thereof to reduce the width of said notch and narrow the opening of said base.

22. The method of claim 21 in which there is the further step of permanently securing said base, while the same is in its deformed state, to the surface of a planar mounting pad.

* * * * *